United States Patent [19]

Suwa et al.

[11] Patent Number: 4,900,538
[45] Date of Patent: Feb. 13, 1990

[54] COMPOSITION FOR INCREASING POTENCY OF ADRIAMYCIN OR DAUNOMYCIN AND REDUCING TOXICITIES THEREOF

[75] Inventors: Yoshihide Suwa; Noriko Kiyota; Hajime Yoshizumi; Shiro Senoh, all of Osaka, Japan

[73] Assignee: Suntory Limited, Osaka, Japan

[21] Appl. No.: 70,155

[22] Filed: Jul. 2, 1987

Related U.S. Application Data

[63] Continuation at Ser. No. 643,325, filed as PCT JP83/00457 on Dec. 27, 1983, published as WO84/02527 on Jul. 5, 1984, abandoned.

[30] Foreign Application Priority Data

Dec. 27, 1982 [JP] Japan ................... 57-229322

[51] Int. Cl.$^4$ ................ A61K 33/04; A61K 31/70
[52] U.S. Cl. ..................... 424/10; 424/164; 514/34
[58] Field of Search ............... 424/10, 164; 514/34

[56] References Cited

U.S. PATENT DOCUMENTS 4,327,083 4/1982 Alvarez ................. 424/162
4,548,927 10/1985 Eaton ................... 514/34

OTHER PUBLICATIONS

Chemical Abstracts, vol. 83, No. 7, Aug. 8, 1975, p. 46, Abstract 53458a, Columbus, OH, U.S. by K. Handa et al.

Abstract and Chemical Abstracts, Ninth Collective Index, Chemical Substances, pp. 23962–23963, in relation to 83:53458a.

Chemical Abstracts, vol. 98, No. 5, Jan. 31, 1983, p. 548, Abstract 33245k, Columbus, OH, U.S., Y. Suwa et al.

Chemical Abstracts, vol. 93, No. 25, Dec. 22, 1980; p. 204, Abstract 232249m, Columbus, OH, U.S., A. DiMarco et al.

Chemical Abstracts, vol. 67, No. 13, Sep. 25, 1967; p. 5877, Abstract 62632g, Columbus, OH, U.S., A. DiMarco et al.

Kirk Othmer, Encyclopedia of Chemical Technology, vol. 19, 1969.

Primary Examiner—Jerome D. Goldberg
Attorney, Agent, or Firm—Cushman, Darby & Cushman

[57] ABSTRACT

The present invention provides a composition comprising adriamycin or daunomycin in mixture with one or more compounds selected from sulfite, acid sulfite, pyrosulfite, diothionite and sulfurous anhydride in order to reduce the toxicities of adriamycin or daunomycin and to increase the potency thereof and a method comprising administering said compounds in mixture with adriamycin or daunomycin.

By the composition and method of the present invention the safe and effective treatment of various tumors with adriamycin and daunomycin, which have remarkably high potency, but also have serious side effects, will be provided.

4 Claims, 9 Drawing Sheets

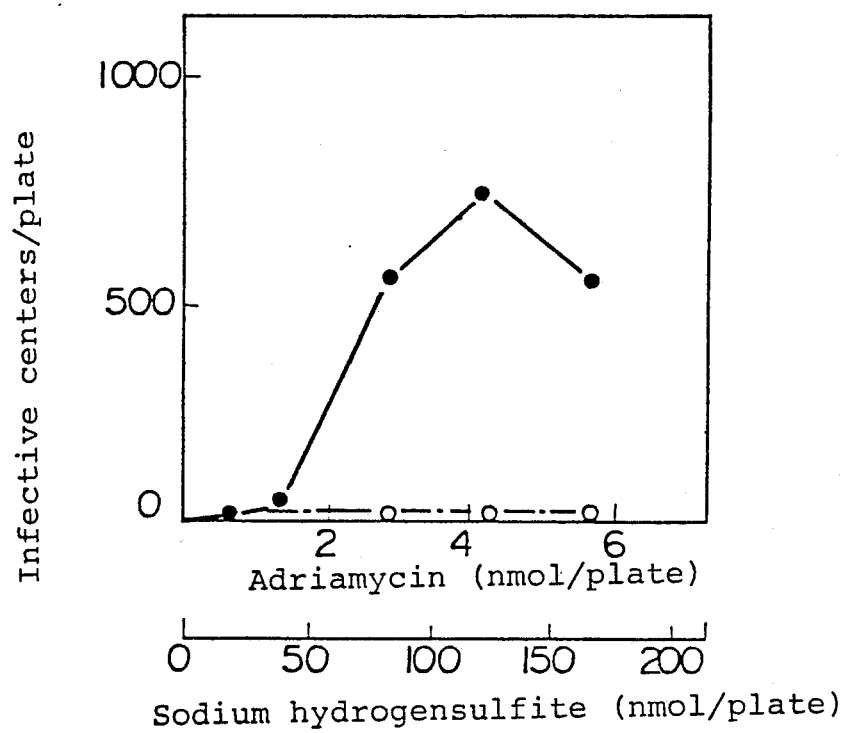
F I G. 3
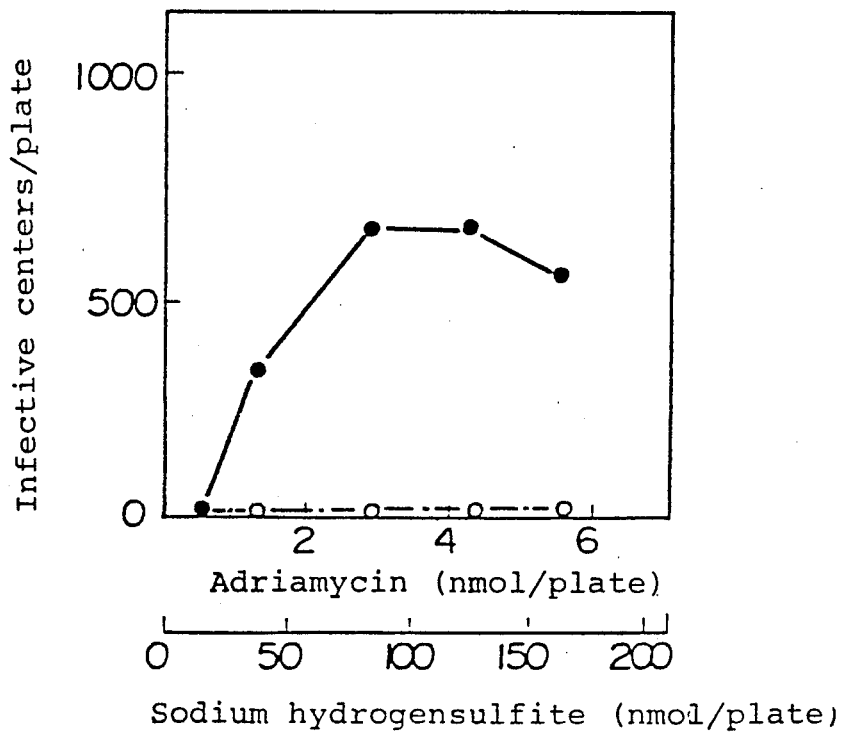
F I G. 4

F I G. 5
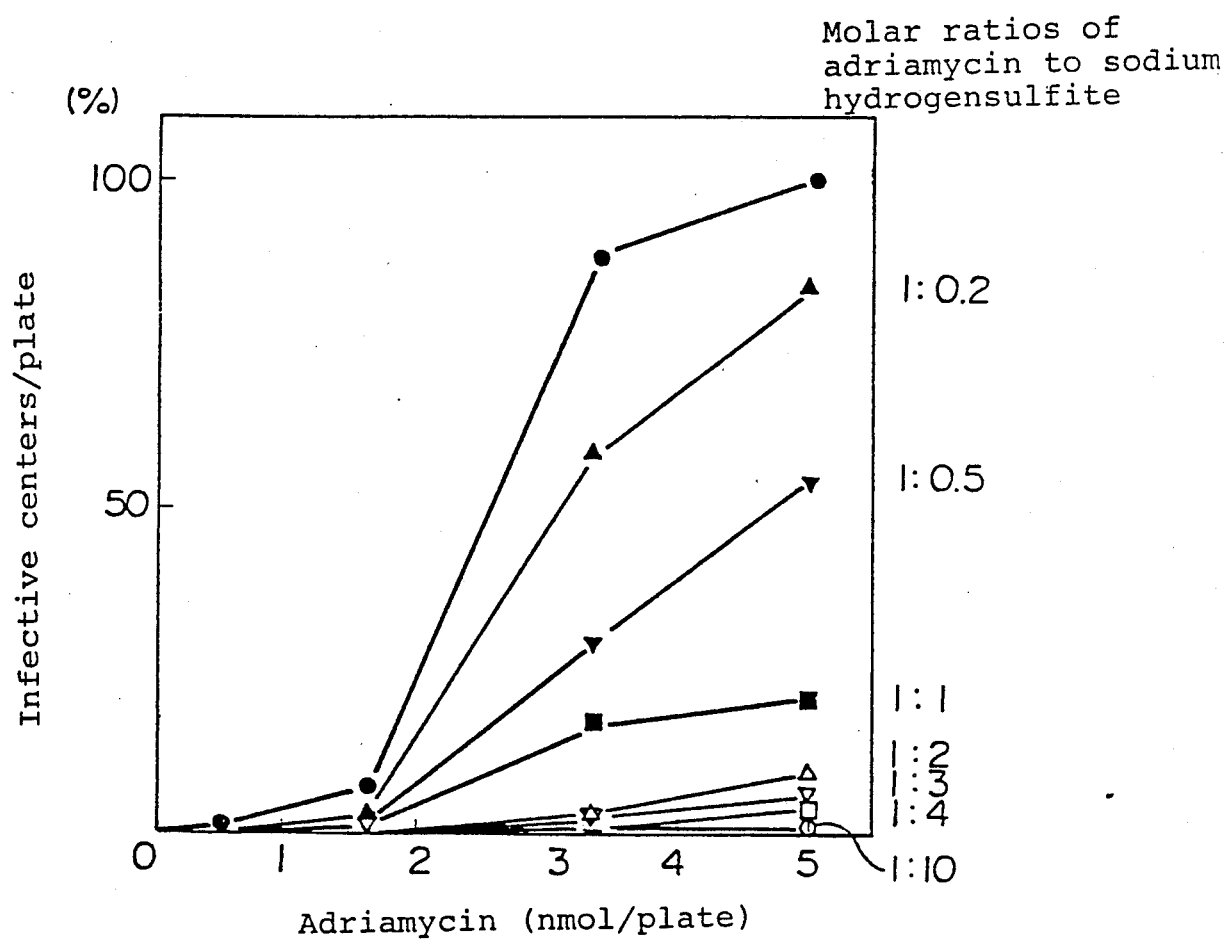

F I G. 13
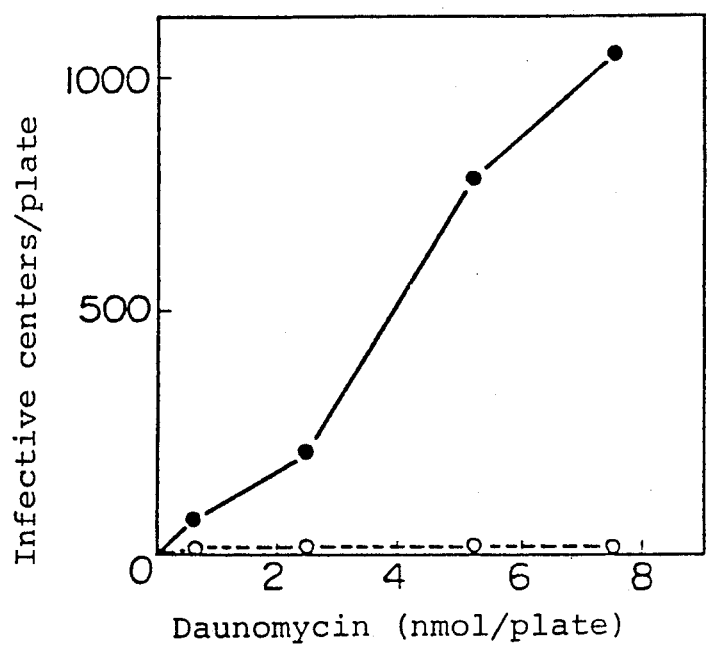
F I G. 14
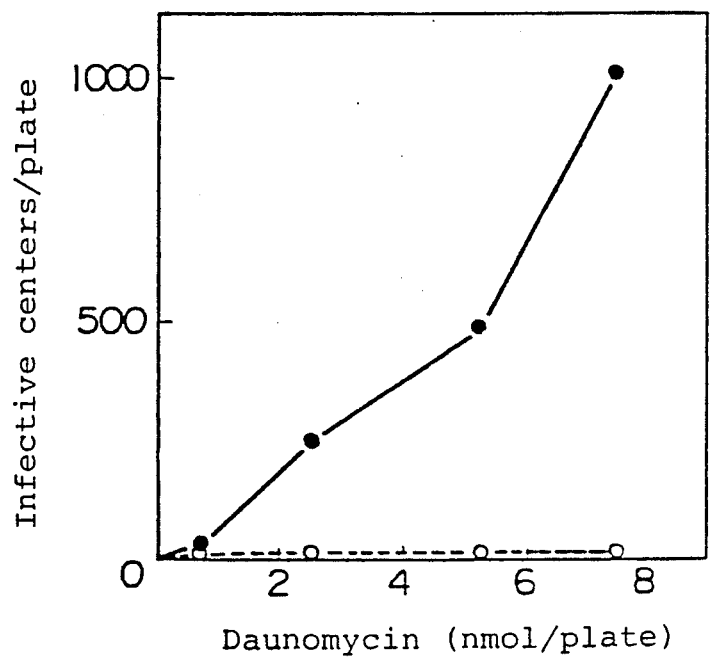

COMPOSITION FOR INCREASING POTENCY OF ADRIAMYCIN OR DAUNOMYCIN AND REDUCING TOXICITIES THEREOF

This application is a continuation of application Ser. No. 645,325, filed as PCT JP83/0457 on Dec. 27, 1983, published as WO84/02527 on Jul. 5, 1984, now abandoned.

Field of the Invention

The present invention relates to a composition for increasing the anti-carcinogenic activity of adriamycin or daunomycin and reducing side effects caused by them.

Prior Art

Currently agents which react with intracellular DNAs are the main stream of agents for treating cancers. However, carcinostatic agents which attack said DNAs have side effects such as cardiotoxicity, hepatotoxicity, nephrotoxicity and hematogeneous obstacles. Moreover, the carcinostatic agents have mutagenicity and some of them (e.g. adriamycin and daunomycin) have been proved to be carcinogenic. From the above facts there is fear that secondary carcinogenesis occurs after treating cancers with such carcinostatic agents. Therefore, reduction of side effects including mutagenicity is a main theme in the development of carcinostatic agents and treatment of cancers.

Suwa, one of the inventors, investigated the inactivation of mutagenicity of beverages (both alcoholic and nonalcoholic, e.g. coffee) and tobacco and discovered factors for inactivating mutagenicity and disclosed said factors and safe beverages (both alcoholic and non-alcoholic) and tobacco, and foods in Japanese Patent application No. 144272/81. In this application it is disclosed that sulfite ion or hydrogensulfite ion inactivates mutagenicities of coffee, tobacco tar and spirits.

The inventors searched for a method of inactivation of mutagenicities of carcinostatic agents and succeeded in creating a composition comprising adriamycin or daunomycin as an active ingredient the mutagenicity of which is reduced. Further, according to the present invention, reduction of acute toxicity and remarkable increase in anti-carcinogenic activity, as well as reduction of mutagenicity, can be attained. In result, the range of effective dose of adriamycin or daunomycin was expanded in comparison with adriamycin or daunomycin alone and therefore more an effective treatment of cancer has become possible.

Disclosure of the Invention

The present invention relates to an agent and method for increasing anti-tumor activity of a carcinostatic agent selected from adriamycin and daunomycin and for reducing toxicity and includes administration of said carcinostatic agent in combination with a compound for increasing the potency of the carcinostatic agent and reducing its toxicity which is selected from the group consisting of sulfite, acid sulfite, pyrosulfite, dithionite and anhydrous sulfite and is referred to hereafter as "a sulfite compound". Adriamycin is alternatively named doxorubicin (U.S. Pat. No. 3,590,028), and daunomycin is also named daunorubicin (GB Patent No. 1,003,383). These antibiotics are anthracyclinic antibiotics.

Daunomycin was isolated from a culture of *Streptomyces peuceticus* (A. Grein, C. Spalla, A. Di Marco & G. Canevazzi: Giorn. Microbiol., Vol. 11, 109, 1963). Adriamycin was initially synthesized from daunomycin and subsequently isolated from a culture of a mutant of *Streptomyces peuceticus, Streptomyces peuceticus var. caesius* (F. Arcamone, G. Cassinelle, G. Fantini, A. Grein, P. Orezzi, C. Pol & C. Spalla: Biotechnol. Bioeng., Vol. 11, 1101, 1969). Both adriamycin and daunomycin react with 3 base pairs of DNA per one molecular (intercalation). Therefore, the effects of these antibiotics are considered to be mainly due to the inhibition of RNA and DNA polymerases which use DNA as a mould. Incidentally, there is a report that DNA cleavage induced by free radicals such as quinone radicals (.AH) which are produced by reductive oxidation of the quinone moieties, $O_2^-$ and OH, contributes to anti-tumor activities. These antibiotics can be adapted for acute or chronic leukemia, carcinoma, sarcoma, lymphoma malignum etc. However, said antibiotics have side effects such as vomiturition, vomition, pyrexia, epilation, depression of bone marrow etc. and one particular side effect, cardiotoxicity, is severe. Therefore it is earnestly desired to reduce the side effects of these antibiotics.

On the other hand, sulfite ion and hydrogensulfite ion are produced in vivo, for example, by isomerization of sulfur containing amino acid and an adult excretes daily into urine an amount of said ions equal to about 2 g (Institute of Food Technologists and Committee on Public Information, Nutr. Rev., Vol. 34, 58, 1976). Moreover, in vivo sulfite ion and hydrogensulfite ion are attached by sulfite oxidase which is present in liver as a mechanism of detoxication and have often been proved not to be carcinogenic (for example, refer to H. P. Til, V. J. Feron & A. P. DeGroot: Food Cosmet. Toxicol., Vol. 10, 291, 463, 1972). Incidentally, sulfite compounds have been added to beverages and foods and are appreciated as safe additives because they were not listed in "List of food additives which are associated with chromosome aberration" published by the National Institute of Hygenic Science in 1981.

The inventors used sulfite compounds whose safeties had been established with regard to reduction of mutagenicity and toxicity of carcinostatic agents and increases in their anti-tumor activities.

When mixing an anthracyclinic carcinostatic agent with a sulfite compound the preferable ratio by weight of the former to the latter is 1:2–900. This ratio can be used when administering them. By using the above mixture index of life spread (ILS; %) is remarkably increased in comparison with the use of adriamycin or daunomycin alone.

BRIEF EXPLANATION OF THE DRAWINGS

The present invention is further illustrated by the drawings accompanying the specification.

FIGS. 3 and 4 are graphs showing the effects of sodium hydrogensulfite on the phage inducing activity of adriamycin in relation to S9 mix. FIG. 3 shows said activity in the absence of S9 mix and FIG. 4 shows it in the presence of S9 mix.

In each figure the symbol ●—● indicates adriamycin alone, the symbol O--O indicates adriamycin plus sodium hydrogen sulfite.

FIG. 5 is a graph showing the mol ratios of adriamycin to sodium hydrogensulfite required to reduce mutagenicity of adriamycin in the absence of S9 mix. In this figure the symbols ▲, ▼, ■ △, ▽, □ and O indicate mol ratios of adriamycin to sodium hydrogensulfite 1:0.2, 1:0.5, 1:1, 1:2, 1:3, 1:4 and 1:10, respectively and the symbol ● indicates adriamycin alone.

Figure 6:
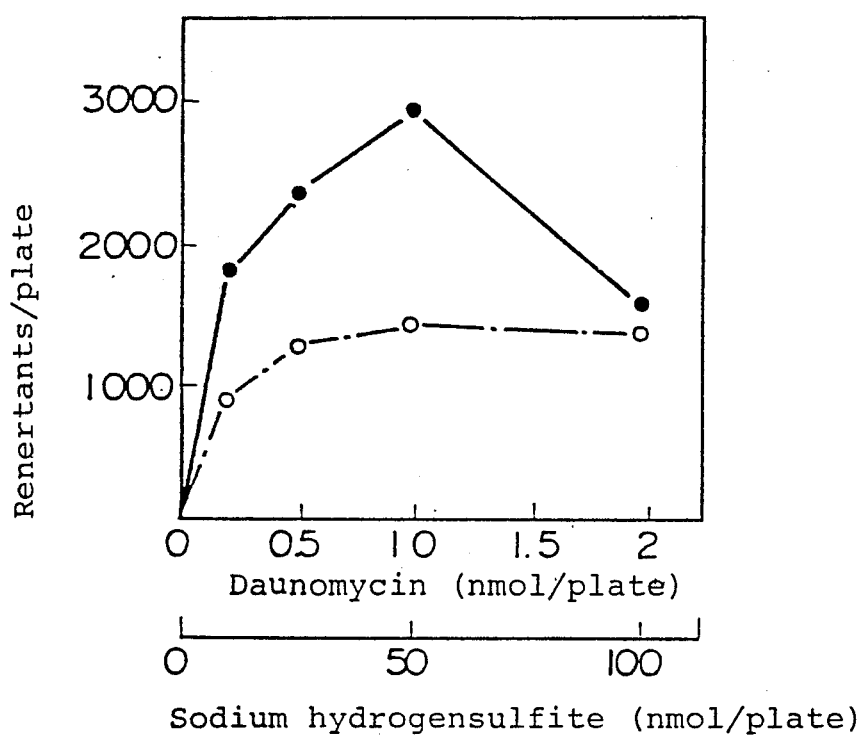
Figure 7:
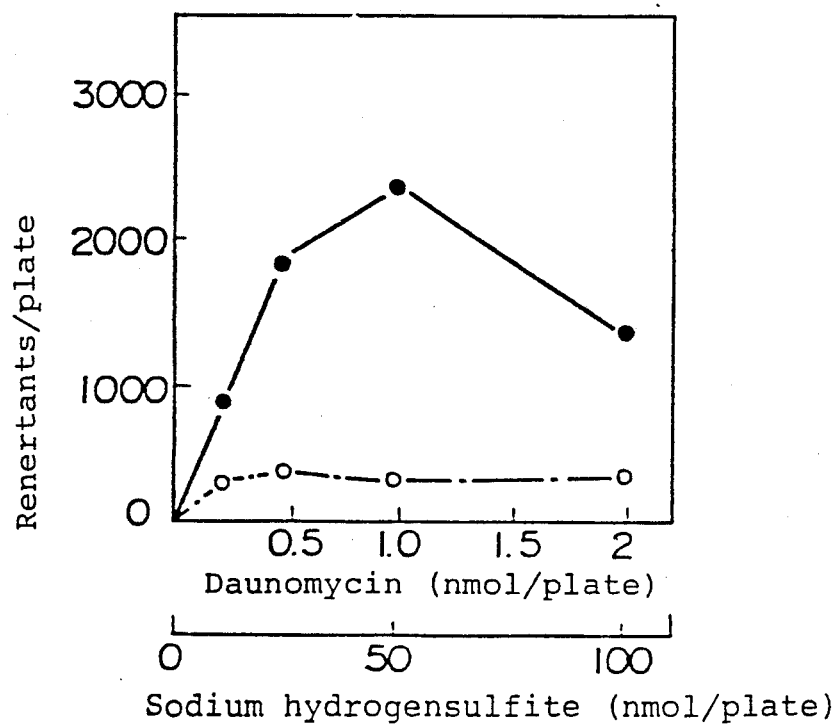

FIG. 6 is a graph showing the effects of sodium hydrogensulfite on mutagenicity of daunomycin assayed by Ames test using *Salmonella typhimurium* TA 98 strain in the absence of S9 mix and FIG. 7 is a graph showing the effects in the presence of S9 mix.

Figure 8:
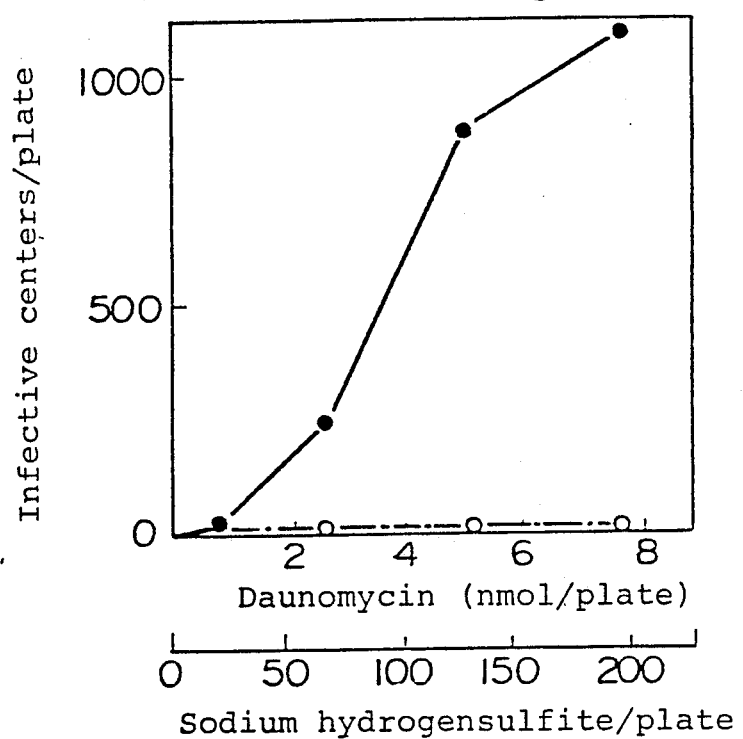
Figure 9:
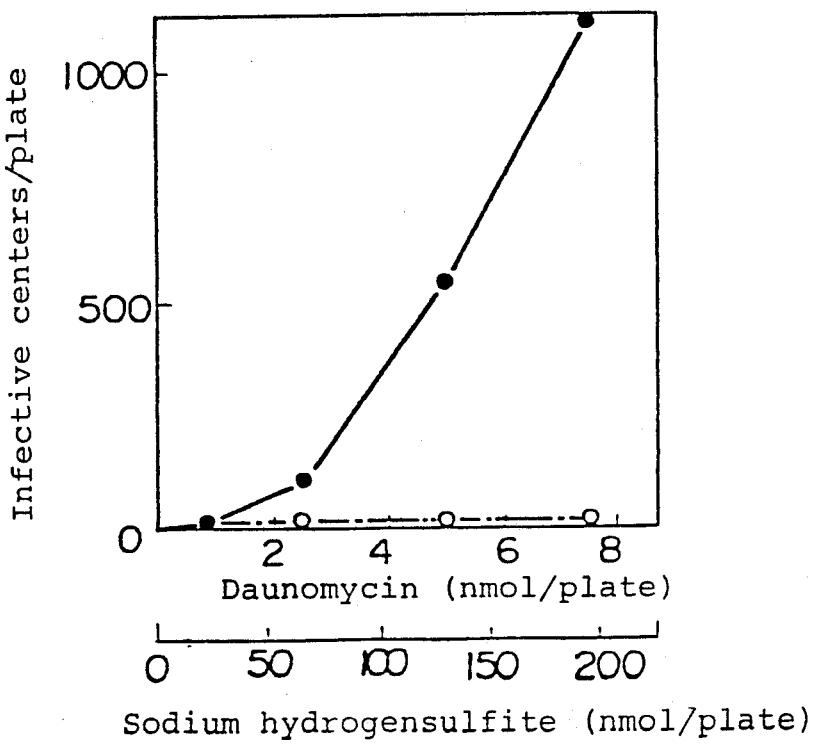

FIG. 8 is a graph showing the effects of sodium hydrogensulfite on mutagenicity of daunomycin assayed by Inductest in the absence of S9 mix and FIG. 9 is a graph showing the effects assayed in the presence of S9 mix. In each figure the symbol ●-● indicates daunomycin alone and the symbol O--O indicates daunomycin plus sodium hydrogensulfite.

Figure 10:
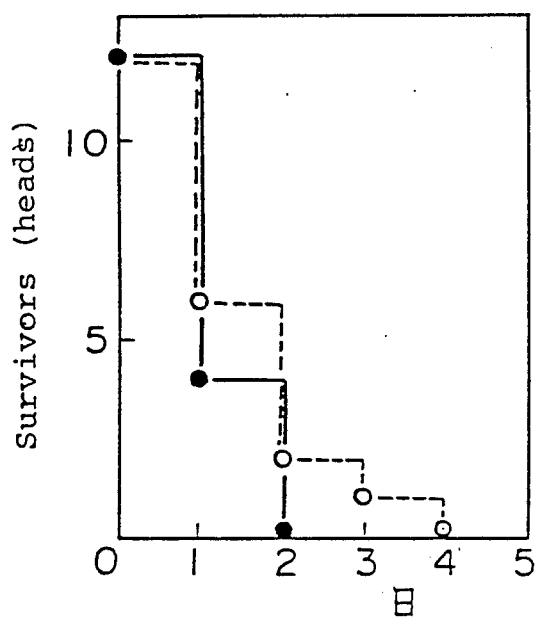

FIG. 10 is a graph indicating survivors to show the effects of sodium hydrogensulfite (53.3 mg/kg) on toxicity of adriamycin when intraperitoneally administered to mice at a daily dose of 20 mg/kg for 3 days. In this figure the symbol ●-● indicates adriamycin alone and the symbol O-O indicates adriamycin plus sodium hydrogensulfite.

Figure 11:
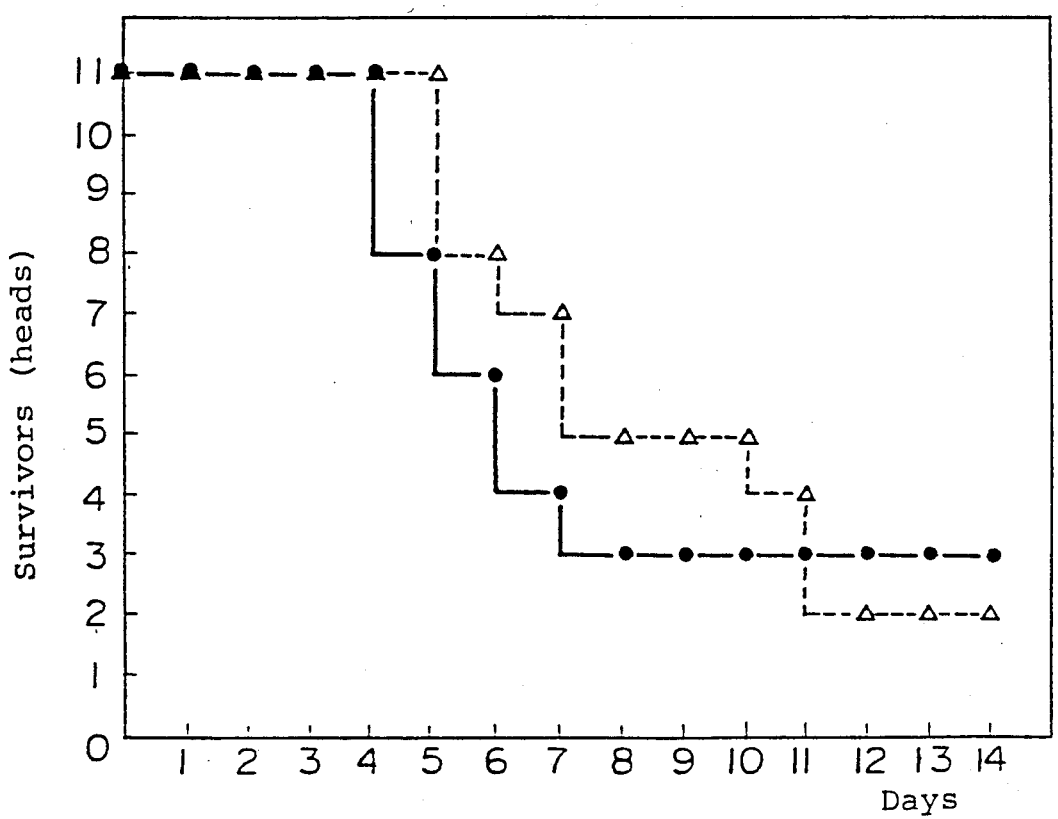

FIG. 11 is a graph showing the effects of sodium hydrogensulfite (100 mg/kg) on toxicity of adriamycin when administered to mice in daily dose of 20 mg/kg. In this figure the symbol ●-● indicates adriamycin alone and the symbol △-△ indicates adriamycin plus sodium hydrogensulfite.

Figure 12:
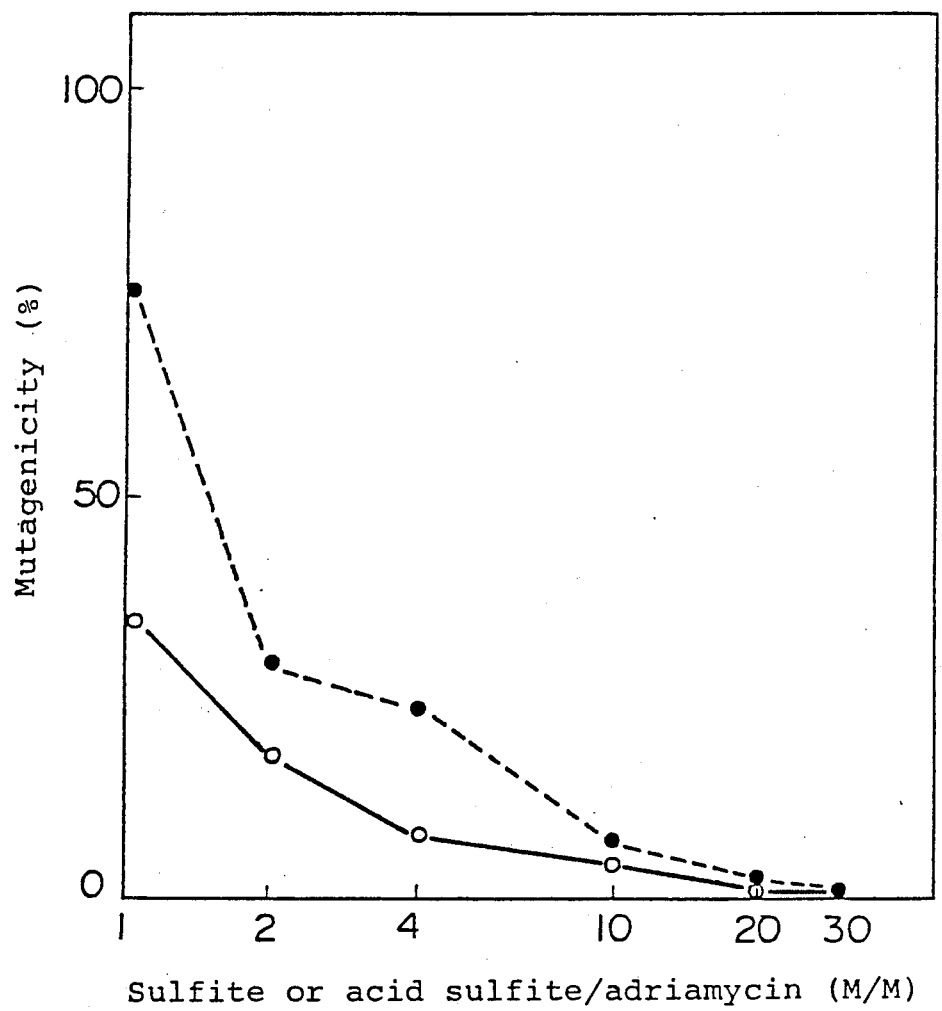

FIG. 12 is a graph showing the relationship between dose and effects of sulfite or acid sulfite on the inactivation of mutagenicity of adriamycin assayed by Inductest III in the absence of S9 mix. In FIG. 12 the symbol indicates adriamycin plus sulfite and the symbol indicates adriamycin plus acid sulfite.

FIGS. 13 and 14 are graphs showing the inactivation of mutagenicity of daunomycin by sodium dithionite assayed by Inductest III in the absence of S9 mix. In these figures the symbol ●-● indicates daunomycin alone and the symbol O-O indicates daunomycin plus sodium dithionite.

Figure 15:
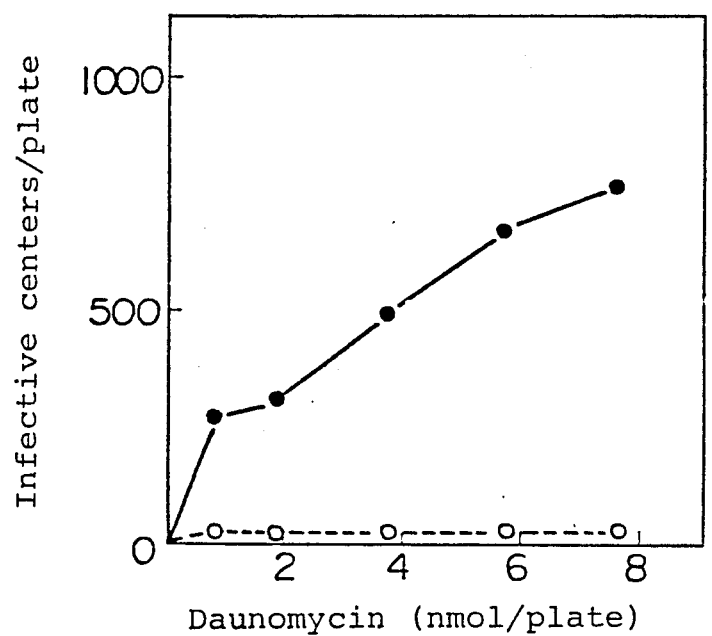
Figure 16:
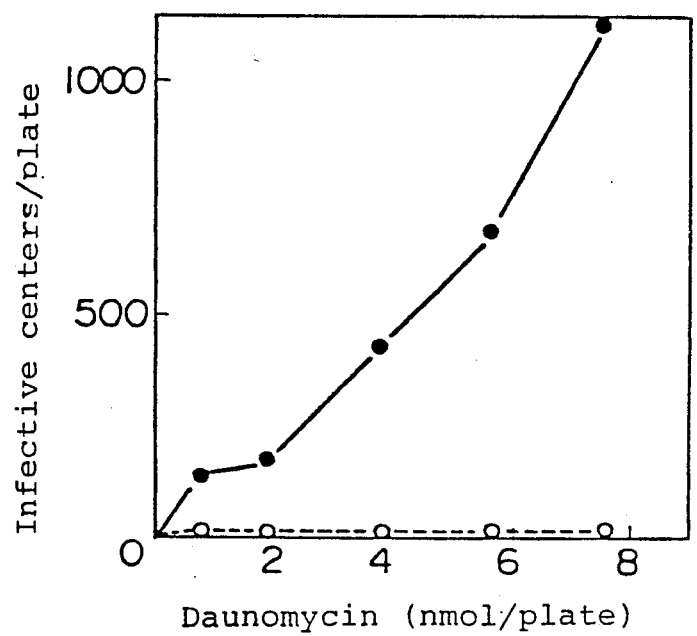

FIGS. 15 and 16 are graphs showing the inactivation of mutagenicity of daunomycin by sodium sulfite assayed by Inductest III in the absence or presence of S9 mix. In these figures the symbol ●-● indicates daunomycin alone and the symbol O--O indicates daunomycin plus sodium sulfite.

THE BEST EMBODIMENTS FOR PRACTICE OF THE INVENTION

EXAMPLE 1

Inactivation of mutagenicity of carcinostatic agents

Method for Determining Mutagenicity and Effects of Control of Mutagenicity (1) Method i:

This method is based on the Ames test (B. N. Ames, J. Mac Gann and E. Yamasaki: Mutation Research, Vol. 31, 347-364, '75). In this example, the Preincubation Method, which is an improved process of the Ames test, was used (Sugimura and Nagao: Chemical Mutagens, Vol. 6, p 40, 1981). The strain used in this method was histidine requisite *Salmonella typhimurium* TA 100 and TA 98 (hereinafter referred to as St TA 100 and St TA 98).

Method ii:

Inductest III (P. Morean, A. Bailone and R. Devoret: Proc. Natl. Acad. Sci. U.S.A., Vol. 73, No. 10, 3700-3704, '76). This method is a test for mutagenicity using prophage λ induction as an index. The strains used in this method were *Escherichia coli* K 12 envA uvr B (λ), GY 5027 and as λ indicator GY 4015 ($A_{mp}R$). Incidentally, in this example the incubation period of 20 minutes in Inductest III was changed to 40 minutes to improve reproductivity.

(2) Preparation of samples

Adriamycin or daunomycin was dissolved in aseptic distilled water. At the same time, predetermined amounts of sodium sulfite, sodium hydrogensulfite (sodium acid sulfite), sodium pyrosulfite, sodium dithionite or sulphurous anhydride were dissolved in aseptic distilled water. Each solution was mixed with an equivalent volume of the solution of adriamycin or daunomycin to make 100 μl directly or, after dilution with distilled water, 50% aqueous DMSO solution and carcinostatic agents to which no sulfite compound is added, were used.

(3) Measurement of mutagenicity:

Method i: Ames test:

To 100 μl of each of the samples prepared in the above (2), 500 μl of 100 mM sodium phosphate buffer (pH 7.4) and 100 μl of a culture of St TA 100 or St TA 98 were added. Each mixture was shaken for 20 minutes at 37° C., added to 2.5 ml of a soft agar solution and spread on 0.1% glucose agar plate which had been supplemented with 0.1 μM per plate of histidine in order to create several divisions. After incubation at 37° C. for 48 hours, the number of colonies on the plate was counted as revertants. This method uses nutrient requisiteness of the above strains as an index.

Method ii: Inductest III:

To 100 μl of each of the samples prepared in the above (2), 0.1M sodium phosphate buffer (pH 7.4 and 100 μl of a culture of *Escherichia coli* K12 (GY 5027 strain above-mentioned) were added. These mixtures were shaken at 37° C. for 40 minutes with shading. To the mixture 200 μl of a culture of GY 4015 strain and 2.5 ml of a soft agar solution were added and thoroughly stirred. The mixture was spread on GT-amp plate (P. Moreau et al., Proc. Hatl. Acad. Sci. U.S.A., Vol. 73, No. 10, 3700-3704, '76). After standing at 37° C. overnight, prophage λ induction activity was measured by counting plagues on the plate. This method uses phage induction activity as an index.

RESULTS AND ANALYSIS

Figure 1:
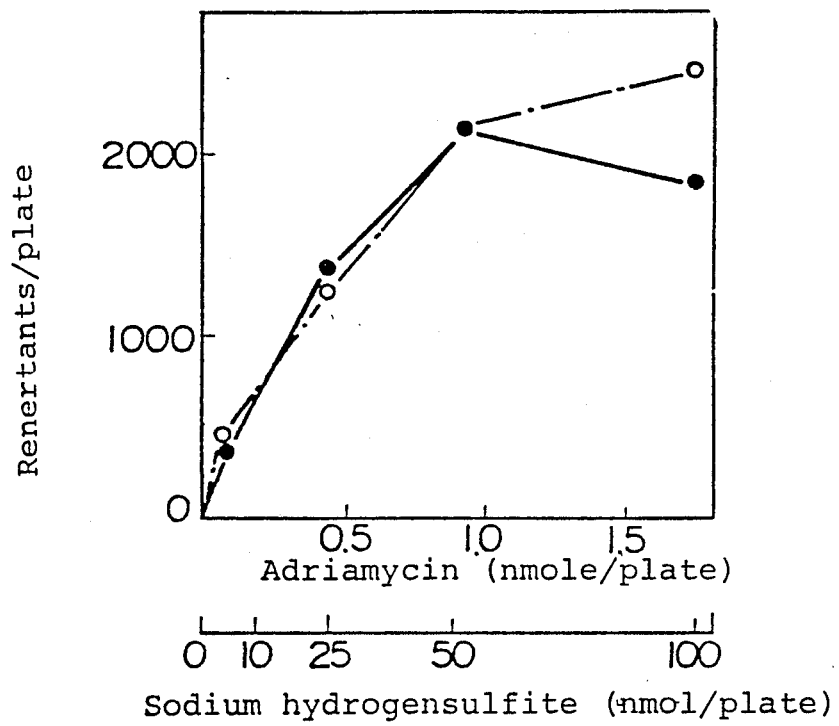
FIG. 1 is a graph showing change of mutagenicity of adriamycin against *Salmonella typhimurium* TA 98 strain in the absence of rat liver homogenate (S9 mix) after addition of sodium hydrogen sulfite and FIG. 2 is one showing the change of mutagenicity of adriamycin as mentioned above in the presence of rat liver homogenate (S9 mix).
Figure 2:
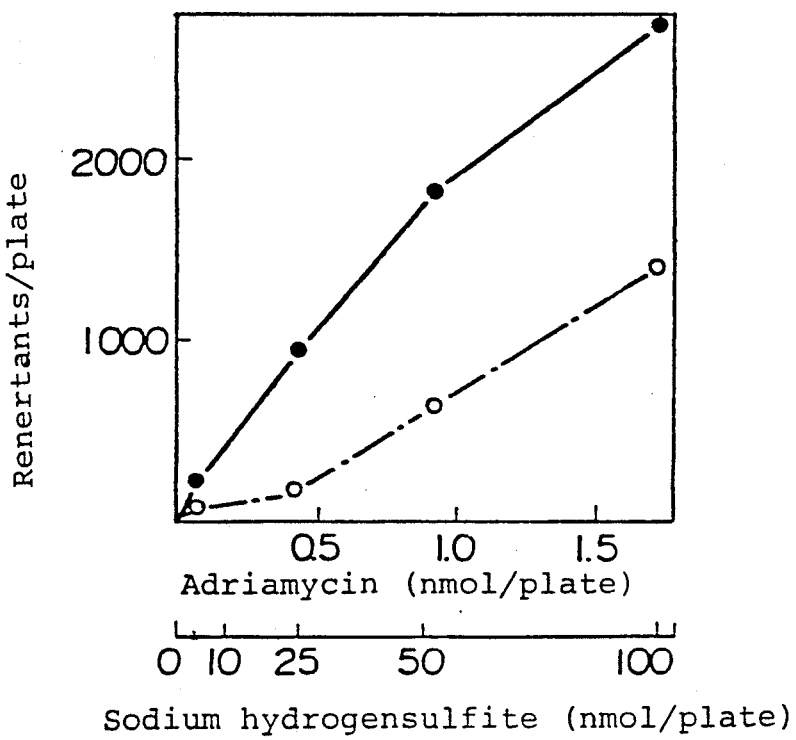

First, the way in which the mutagenicity of adriamycin against *Salmonella typhimurium* TA 98 is changed by adding sulfite compounds was studied in relation to the S9 mix. As a result, it was found that the sulfite compounds were not effective in the absence of S9 mix (FIG. 1) but reduced the mutagenicity of adriamycin by half (FIG. 2). This means that the addition of sulfite compounds stimulated metabolism and detoxication in the liver.

Next, phage inductive activity of adriamycin was completely inactivated by adding the sulfite compounds independently of S9 mix (FIGS. 3 and 4). Differences between the results obtained by the Ames test and those obtained by the Inductest III are recognized to be due to differences in the mechanisms of the mutations caused by these test methods. In FIG. 5, the amounts of hydrogensulfite ion (mol ratios of adriomycin to sodium hydrogensulfite) required for reducing mutagenicity of adriamycin were shown. Hydrogensulfite ion inactivated the mutagenicity even at a mol ratio of 1:0.2 in the absence of S9 mix. But, it was found that at least ten times as much hydrogensulfite ion in molar concentration was necessary for complete inactivation.

Next, the effects of sulfite compounds on the mutagenicity of daunomycin were studied. In the Ames test wherein *Salmonella typhimurium* TA 98 was used, the sulfite compounds inactivated about 50% and about 85% of the mutagenicity of daunomycin in the absence and presence of S9 mix, respectively (FIGS. 6 and 7). In the Inductest III, the sulfite compounds completely inactivated phage inductive activity of daunomycin independently of S9 mix (FIGS. 8 and 9).

In the above experiments the sulfite compounds didn't inhibit the growth of the strains used and therefore, the reduction of mutagenicity was not due to the death of said strains. On the other hand, the mutagenicities of both adriamycin and daunomycin per se appear to be reduced at high levels as shown by FIGS. 1, 3 and 4, and 6 and 7. However, this represents the apparent reduction of mutagenicity due to reduction in the numbers of survival cells because both of the anthraquinone antibiotics have cellular toxicity.

Incidentally, the above inactivation of mutagenicity was not observed for sulfate ion.

EXAMPLE 2

Reduction of toxicity of carcinostatic agents

Measurement of Acute Toxicity

Male CD-1 (ICR) mice (12 weeks old) were used as test animals. The temperature in the animal room was maintained at 23° C. (±3° C.) and relative humidity was kept at 30–70%. Artificial lighting was carried out by illumination and darkening at successive intervals of 12 hours.

CE-2 (Trademark of an animal foodstuff available from Nihon Kurea Kabushiki Kaisha, Meguro-ku, Tokyo, Japan) was freely taken. The test substances were dissolved in distilled water and intraperitoneally administered to the animals at a dose of 10 ml/kg.

Results and Analysis (1) First, A group of 12 male CD-1 mice to which 20 mg/kg of adriamycin was daily intraperitoneally administered for 3 days was used as a control group. To each of the other group of 12 animals an aqueous sodium hydrogensulfite solution (53.8 mg/kg) was administered 30 minutes before and one hour after administering adriamycin. FIG. 10 shows a graph showing survivors obtained from the above experiments.

Effects of sodium hydrogensulfite were determined by t-test from survival days of mice in each group shown in FIG. 10. As a result sodium hydrogensulfite significantly reduced toxicity at a confidence level of 90%.

The above t-test was carried out as follows. Survival days of the animals used in the above experiments were tabulated as follows:

| Mouse No. | 1 | 2 | 3 | 4 | 5 | 6 | 7 | 8 | 9 | 10 | 11 | 12 | $\bar{x}$ | s |
|---|---|---|---|---|---|---|---|---|---|---|---|---|---|---|
| A (No hydrogensulfite was administered) | 0 | 0 | 0 | 0 | 0 | 0 | 0 | 0 | 1 | 1 | 1 | 1 | 0.3333 | 0.5778 |
| B (Hydrogensulfite was administered) | 0 | 0 | 0 | 0 | 0 | 0 | 1 | 1 | 1 | 1 | 2 | 3 | 0.75 | 1.1903 |
| B-A | 0 | 0 | 0 | 0 | 0 | 0 | 1 | 1 | 0 | 0 | 1 | 2 | 0.4167 | 0.7638 |

B-A can be considered to follow normal distribution $N(\mu, \sigma^2)$. If it is hypothesized that A and B are the same, $H:\mu=0$. Since $\sigma^2$ is not definite, t-test is used. Since $x=0.4167$, $s=0.7638$ and $\nu=12-1=11$ $$|t| = \frac{|0.4167 - 0|}{0.7638/\sqrt{12-1}} \approx 1.8094 < 2.201 = t_{0.05}.$$

Therefore, A and B cannot be considered to be different. (When $\nu$ is 11, $t_{0.05}=2.201$)

$$\left( \because \text{If } \frac{|\bar{x} - \mu|}{s/\sqrt{n-1}} = \frac{|\bar{x} - \mu|}{\mu/\sqrt{n}} > \frac{t_{0.05}}{t_{0.01}} \text{for } t_{0.05} \text{ and } t_{0.01} \right.$$

when degree of freedom $\nu$ is given by $\nu=n-1$, H is dismissed at a level of significance of $5\%_{01}\%$. Or if not, H is not dismissed.) Since $t_{0.01}=1.796$ there are significant differences between A and B at a confidence level of 90%.

(2) In the same manner as in (1) adriamycin (20 mg/kg) and sodium hydrogensulfite (100 mg/kg) were mixed and intraperitoneally administered. As shown in FIG. 11, toxicity of adriamycin is significantly reduced (confidence level 99%: t-test mode).

Incidentally t-test was conducted as follows:

| | Incidentally t-test was conducted as follows: | | | | | | | | | | | | |
|---|---|---|---|---|---|---|---|---|---|---|---|---|---|
| Mouse No. | 1 | 2 | 3 | 4 | 5 | 6 | 7 | 8 | 9 | 10 | 11 | $\bar{x}$ | s |
| A(ADM*) | 14 | 14 | 14 | 7 | 6 | 6 | 5 | 5 | 4 | 4 | 4 | 7.545 | 2.747 |
| B(AMBS**) | 14 | 14 | 11 | 11 | 10 | 7 | 7 | 6 | 5 | 5 | 5 | 8.636 | 2.939 |
| B-A | 0 | 0 | −3 | 4 | 4 | 1 | 2 | 1 | 1 | 1 | 1 | 1.000 | 1.000 |

*Adriamycin alone,
**Adriamycin + sodium hydrogensulfite

B-A can be considered to follow normal distribution $N(\mu, \sigma^2)$.

If it is hypothesized that A is the same as B, $H:\mu=0$ since $\sigma^2$ is not definite, t-test mode is used.

Since $\bar{x} = 1$, $s = 1$ and $\nu = 11 - 1$ in $|t| =$ $$\frac{|\bar{x} - \mu|}{s/\sqrt{n-1}}, |t| \approx 3.1622.$$

This value is over the value of $t_{0.05}$ 2.228 when degree of freedom $\nu = 10$.

If $\dfrac{|\bar{x} - \mu|}{s/\sqrt{n-1}} > \dfrac{t_{0.05}}{t_{0.01}}$, H is dismissed at a level of significance of 5%₁%. Therefore, acute toxicity of AMBS is significantly low at a confidence level of 95%.

EXAMPLE 3

Increase in in vivo carcinostatic activity

Measurement of Carcinostatic Activity

Male $BDF_1$ mice (57BL/6XDBA/2) weighing 19–20 g were used in this experiment. Feed (CA-1, Nihon Kurea Kabushiki Kaisha, Meguro-ku, Tokyo, Japan) and water were freely taken. $1 \times 10^5$ L 1210 cells were intraperitoneally transplanted to a mouse in each group of 6 mice. Test substances were intraperitoneally administered to mice 24 hours after i.p. injection of L1210 cells and thereafter one time each day for 5 days. Survival days of all of the mice were recorded and carcinostatic effects of the test compounds were measured by using index of life spread (ILS %) to the control group.

Results and Analysis

Adriamycin alone and a solution of a mixture of adriamycin and sodium hydrogensulfite were administered to the mice into which L1210 cells had been transplanted. As shown in Table 1, at dosage levels of 1 mg/day and 3 mg/day of adriamycin, the values of ILS were >194% and 71% respectively and survivors in each group of six mice 60 days after administration of adriamycin were 1 and zero respectively. In the contrast, when sodium hydrogensulfite is simultaneously administered, at a dosage level of adriamycin of 1 mg/day in combination with low dosage levels of sodium hydrogensulfite of 5.4 mg/kg/day and 100 mg/kg/day, the values of ILS were raised to >245% and >374% respectively. And at a dosage level of adriamycin of 3 mg/kg/day in combination with low dosage levels of sodium hydrogensulfite of 5.4 mg/kg/day and 300 mg/kg/day, the values of ILS were increased to >127% and >380% respectively. Moreover, survivors in groups of 6 carcinoma-carrying mice to which adriamycin was administered at a dosage level of 1 mg/kg/day in combination with dosage levels of sodium hydrogensulfite of 5.4 mg/kg/day and 100 mg/kg/day were increased to 2 and 3 respectively. Even at a dosage level of 3 mg/kg/day of adriamycin, combination with sodium hydrogensulfite caused the number of survivors to increase.

TABLE 1

| Adriamycin (mg/kg/day × day) | Sodium hydrogensulfite (mg/kg/day × day) | Survivors (on Day 60) | ILS (%) |
|---|---|---|---|
| 1 × 5 | 0 | 1/6 | >194 |
| 1 × 5 | 5.4 × 5 | 2/6 | >245 |
| 1 × 5 | 100 × 5 | 3/6 | >374 |
| 1 × 5 | 300 × 5 | 1/6 | >153 |
| 3 × 5 | 0 | 0/6 | 71 |
| 3 × 5 | 5.4 × 5 | 1/6 | >127 |
| 3 × 5 | 300 × 5 | 3/6 | >380 |
| 3 × 5 | 900 × 5 | 0/6 | −77 |

(Adriamycin and sodium hydrogensulfite were dissolved in sterilized physiological saline and the solution was intraperitoneally administered at a dose of 10 ml/kg.)

Thus, a mixture of sodium hydrogensulfite and adriamycin exhibited remarkably superior carcinostatic effects in comparison with adriamycin alone.

EXAMPLE 4

In the manner as described in Example 1, the relation between dose and response of sulfite and acid sulfite as to mutagenicity of adriamycin was studied by using Inductest III.

In FIG. 12, percentages of mutagenicity (phage induction activity) of adriamycin in the absence of S9 mix when sulfite or acid sulfite was added at molar ratios to adriamycin of 1:1, 2:1, 4:1, 10:1, 20:1 and 30:1 are shown. In this case, mutagenicity of adriamycin alone was regarded as 100%.

Potassium sulfite was used as a sulfite compound and potassium pyrosulfite which produces 2 equivalents of hydrogensulfite ion when dissolved in water was used as acid sulfite. In FIG. 12 the syumbol ●-● indicates adriamycin plus potassium sulfite and the symbol ○-○ indicates adriamycin plus pyrosulfite.

The higher the proportion of sulfite or acid sulfite became, the more remarkably the mutagenicity of adriamycin was inactivated.

EXAMPLE 5

An experiment wherein the mutagenicity of adriamycin is inactivated by dithionite was conducted by Inductest III (phage induction test) in the absence and presence of S9 mix. Dithionite produces two equivalents of hydrogensulfite ions when dissolved in water.

The molar ratio of sodium dithionite to daunomycin was 15:1. Results in the absence of S9 mix were shown in FIG. 13 and those in the presence of S9 mix were shown in FIG. 14. In FIGS. 13 and 14 the symbol ●-● indicates daunomycin alone and the symbol ○-○ indicates daunomycin plus sodium dithionite.

According to FIGS. 13 and 14, the mutagenicity of daunomycin was completely inactivated at a molar ratio of sodium dithionite to daunomycin of 15:1 independently of S9 mix.

EXAMPLE 6

An experiment wherein the mutagenicity of daunomycin is inactivated by sulfite was conducted by Inductest III (phage induction activity) as described in Example 1 in the absence and presence of S9 mix. Sodium sulfite was used as a sulfite at a molar ratio of sodium sulfite to daunomycin of 30:1. Results in the absence of S9 mix are shown in FIG. 15 and those in the presence of it are shown in FIG. 16. In these figures, the symbol ●-● indicates daunomycin alone and the symbol ○-○ shows daunomycin plus sodium sulfite.

From the figures it is clear that the mutagenicity of daunomycin is completely inactivated by sodium sulfite.

In the above examples, acid sulfite, sulfite, pyrosulfite and dithionite were tested. Among them pyrosulfite and dithionite produce two equivalents of hydrogensulfite ions and therefore are substantially the same as acid sulfite. Additionally sulfurous anhydride becomes sulfurous acid when dissolved in water and therefore is essentially the same as sulfite.

From the above results it can be concluded that the above various sulfite compounds reduce toxicities of anthraquinone antibiotics such as mutagenicity and increase carcinostatic activity to realize simultaneously a reduction in the side effects of the carcinostatic agents and an increase in their effects.

We claim:

1. A pharmaceutical composition comprising an antitumorigenically effective amount of adriamycin or daunomycin, a sulfite compound selected from the groups consisting of sulfite, acid sulfite pyrosulfite, dithionite and sulfurous anhydride and a pharmaceutically acceptable carrier wherein the weight ratio of adriamycin or daunomycin to the sulfite compound is 1:1.8 –100.

2. The composition according to claim 1, wherein said weight ratio of adriamycin or daunomycin to the sulfite compound is 1:5.4–100.

3. The composition according to claim 1 wherein the compound is acid sulfite.

4. The composition according to claim 1 wherein the compound is dithionite.

* * * * *